United States Patent [19]

Gilmer, Jr.

[11] Patent Number: 4,723,540
[45] Date of Patent: Feb. 9, 1988

[54] APPARATUS AND METHOD FOR EXERTING AND MAINTAINING A FORCE BETWEEN TWO BONE MEMBERS

[76] Inventor: Raymond E. Gilmer, Jr., 2881 S. Delaney Ave., Orlando, Fla. 32806

[21] Appl. No.: 885,681

[22] Filed: Jul. 15, 1986

[51] Int. Cl.⁴ .................. A61F 5/04; F16B 15/06; F16B 15/00
[52] U.S. Cl. .................. 128/92 YC; 128/92 V; 128/92 VT; 227/DIG. 1; 411/469; 411/456 411/456
[58] Field of Search ........ 128/92 YC, 92 VT, 92 YF, 128/92 R, 92 V; 227/19, 901, DIG. 1 S, DIG. 1 SC; 411/469, 423, 456

[56] References Cited

U.S. PATENT DOCUMENTS

| | | | |
|---|---|---|---|
| 408,080 | 7/1889 | Carroll | 128/336 |
| 583,455 | 6/1897 | Bush | 128/92 |
| 1,360,421 | 11/1920 | Lloyd | 29/175 R |
| 2,746,451 | 5/1956 | Parker | 128/81 |
| 3,807,394 | 4/1974 | Attenborough | 128/92 |
| 3,900,025 | 8/1975 | Barnes, Jr. | 128/92 |
| 3,969,975 | 7/1976 | Krol | 411/456 |
| 4,009,712 | 3/1977 | Burstein et al. | 128/92 VZ |
| 4,059,102 | 11/1977 | Devas | 128/92 |
| 4,135,505 | 1/1979 | Day | 128/92 |
| 4,263,903 | 4/1981 | Griggs | 128/92 |
| 4,278,091 | 7/1981 | Borzone | 128/334 |
| 4,312,336 | 1/1982 | Danieletto et al. | 128/92 |
| 4,401,112 | 8/1983 | Rezaian | 128/92 |
| 4,414,967 | 11/1983 | Shapiro | 128/92 |
| 4,438,769 | 3/1984 | Pratt et al. | 128/92 YC |
| 4,444,181 | 4/1984 | Wevers et al. | 128/92 |
| 4,445,513 | 5/1984 | Ulrich et al. | 128/69 |
| 4,454,875 | 6/1984 | Pratt et al. | 128/92 |
| 4,475,546 | 10/1984 | Patton | 128/92 |
| 4,488,542 | 12/1984 | Helland | 128/92 |

FOREIGN PATENT DOCUMENTS 1051847 1/1954 France ............................. 128/92

*Primary Examiner*—C. Fred Rosenbaum
*Assistant Examiner*—C. W. Shedd
*Attorney, Agent, or Firm*—Shapiro and Shapiro

[57] ABSTRACT

A bone staple includes a body and a pair of angled arms oppositely threaded into opposite ends of the body. The body has at least one generally flat periphery striking surface and a corresponding relatively sharp outward protrusion at an opposite side of the body from the striking surface. According to the disclosed method, the bone staple is implanted by driving the staple partly into two bone members and then rotating the body to threadably adjust the positions of the arms and thereby exert a force between the bone members. The staple is next driven further by striking the striking surface until the protrusion embeds beneath a bone surface to prevent rotation of the body. A driver tool useful for implanting the staple has a clamping head which receives the staple body and rigidly clamps the angled arms.

16 Claims, 9 Drawing Figures

APPARATUS AND METHOD FOR EXERTING AND MAINTAINING A FORCE BETWEEN TWO BONE MEMBERS

BACKGROUND OF THE INVENTION

The subject invention relates to surgical methods and apparatus for repairing bone injuries and disorders and is more particularly concerned with that aspect of bone repair involving the use of implants. The invention pertains specifically to a bone staple for exerting and maintaining a force between two pieces of bone and to a driver tool useful in implanting the staple. The invention also pertains to a method of implanting a staple of the aforementioned type.

Among their many uses, orthopedic implants are frequently employed for the dual purpose of exerting a force between a pair of bone members to adjust their relative positions and then holding the bone members under pressure so that, over a period of time, they grow to assume their adjusted positions permanently. For example, in the case of bone fractures, implants are often used to place and retain the affected bone fragments in tight compression against each other. This procedure ensures rigid fixation at the fracture site, and thus proper union of the fragments, and accelerates the healing process as well.

SUMMARY OF THE INVENTION

In one of its principal aspects, the invention provides a bone staple which is generally applicable for exerting and maintaining a force between two bone members and which is especially useful for placing and retaining fractures in compression. Generally speaking, a bone staple in accordance with the invention comprises a body which has opposite axially aligned ends threaded in opposite directions, a substantially flat peripheral striking surface, and a relatively sharp outward protrusion disposed laterally across the body from the striking surface. The staple further includes a pair of angled arms threadably engageable with the opposite ends of the body, respectively.

As will be explained more fully hereinafter, the staple utilizes the basic principle of a turnbuckle for adjustment of the relative positions of the angled arms in order to exert a selected force between respective bone members in which the arms have been partially inserted. Following adjustment of the staple, the staple arms are driven further into the respective bone members by hitting a striking surface of the body either directly or indirectly with an impact tool until the protrusion, which is located generally opposite the striking surface, embeds beneath a bone surface (perhaps in a complementary osteotomized recess). So embedded, the protrusion prevents rotation of the staple body and, consequently, any change in the force exerted by the staple arms. In a preferred embodiment, the staple includes three striking surfaces defined by respective sides of a triangular portion of the body, each striking surface having a corresponding protrusion formed at an opposite side of the body by the junction area of the two remaining striking surfaces.

It has been found in trial applications of the inventive staple that it may be especially advantageous in certain cases to hold the angled arms fixed relative to each other as the staple is initially implanted, prior to adjustment. Hence, another major aspect of the invention pertains to a tool suitable for this purpose. More particularly, the invention provides a tool for holding and driving a bone staple of a type having a generally central body with opposite ends and a pair of angled arms respectively receivable by the opposite ends of the body and rotatable on an axis extending between the ends of the body when so received. The tool includes first and second members defining a clamping head having two pairs of opposed jaws adjacent opposite ends of a recess configured to receive the staple body. The tool further includes means cooperable with the clamping head defining members for urging the opposed jaws together to clamp the angled arm members rigidly.

A further major aspect of the invention pertains to a staple and driver tool combination, the staple and driver having the characteristics described in the preceding paragraph.

According to yet another major aspect of the invention, there is provided a method for exerting and maintaining a force between two bone members. The method comprises the steps of providing a bone staple which includes a body having laterally outward protrusion means and which further includes a pair of angled arms oppositely threaded to opposite axially aligned ends of the body, with end portions of the arms freely extending laterally beyond the periphery of the body; partially inserting the end portions of the arms into respective bone members; rotating the staple body to threadably adjust the relative positions of the arms axially of the body; and further inserting the end portions of the arms within the respective bone members and embedding the protrusion means of the body beneath a bone surface.

The features and advantages of the invention will be more fully appreciated from the following description of the preferred embodiments taken in conjunction with the accompanying drawings.

DESCRIPTION OF THE PREFERRED EMBODIMENTS

Figure 2:
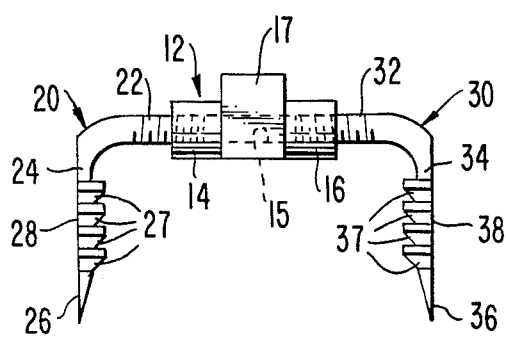
FIG. 2 is a side elevation view of the staple of FIG. 1 with the staple arms in an open or spread condition.
Figure 3:
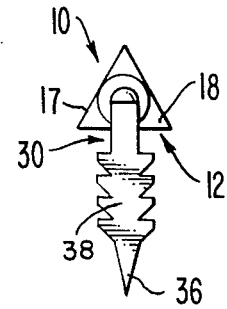
FIG. 3 is an end view of the staple.

Referring now to the drawings, FIGS. 2 and 3 depict a preferred bone staple 10 in accordance with the invention. The staple includes a generally central body 12 and a pair of angled arms 20,30 received by opposite axial ends 14,16 of body 12, respectively. Staple 10 may be made of any appropriate surgical material, such as titanium, which is of suitable strength and rigidity to perform the functions hereinafter described.

In the form shown, body 12 is constructed as a turnbuckle, having an internal axial bore 15 extending betweens its opposite ends 14,16. Bore 15 is internally threaded at the opposite ends of the body, as shown particularly in FIG. 2. The ends of bore 15 are threaded in opposite directions. Arms 20,30 have respective externally threaded ends 22,32 threadably received in the opposite ends of body 12. It will be appreciated that the relative positions of the angled arms 20,30 may be adjusted axially of body 12 simply by rotating the body on its axis about the received arm ends—rotation in one direction causing the arms to move apart and rotation in the opposite direction causing the arms to move toward each other.

In order that the staple may be implanted, arms 20,30, which are substantially right angular in the illustrative embodiment, have respective freely extending portions 24,34. These portions project laterally beyond the periphery of body 12 for impaction or otherwise being inserted into corresponding bone members in a manner to be explained shortly. To facilitate impaction, the extensions 24,34 have respective sharpened tips 26,36. For most applications, the staple is contemplated for permanent implantation in the patient, and the extensions 24,34 are therefore provided with bone engaging serrations, such as barbs 27,37, to prevent the extensions from backing out of the associated bone members once the staple has been implanted. The illustrative staple 10 is designed for the purpose of compressing bone fractures, and the barbs 27,37 are thus disposed only on the inner sides of the associated extensions to grip the associated bone fragments as the staple arms are drawn together. The outer sides 28,38 of the extensions are smooth and flattened to reduce bulk.

In accordance with an important aspect of the invention, body 12 of the staple has at least one relatively flat striking surface, as at 17, with a relatively sharp outward protrusion disposed laterally across the body from the striking surface, as at 18. The striking surface facilitates implantation of the staple by providing an impact surface which may be struck, either directly or indirectly, with an appropriate tool to drive arm extensions 24,34 into respective bone members. The protrusion, as will be explained in more detail shortly, acts to prevent rotation of body 12 once the staple has been fully implanted. Preferably, as in the exemplary embodiment, body 12 has three striking surfaces facing outwardly in different directions and defined by respective sides of a triangular peripheral portion of the body. A corresponding outward protrusion is formed opposite each striking surface by the junction region of the remaining two surfaces, each junction region providing a sharp axial edge portion on the body. To avoid confusing the drawings, only one of the three striking surfaces (17) and the corresponding protrusion (18) have been specifically designated with reference numerals. In the illustrative staple 10, body 12 is generally cylindrical, with the triangular portion being constituted by an enlarged central portion of the body. This offers certain advantages in practice which will be discussed shortly.

Figure 1:
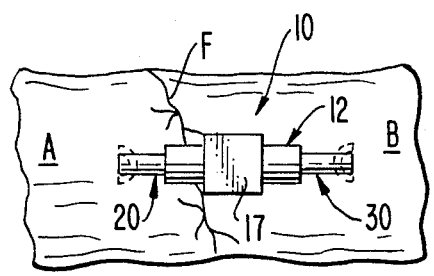
FIG. 1 is a plan view showing a bone staple according to the invention implanted to repair a fractured bone.
Figure 4:
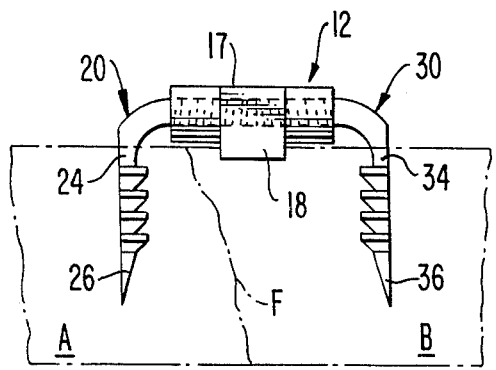
FIG. 4 is a side elevation view of the staple with the staple arms drawn in, as for compressing a fracture site.

The following discussion provides a procedure for implanting the staple in the exemplary context of bone fracture repair and will serve to illuminate the functional significance of the various features of staple 10 described above. FIGS. 1 and 4 depict staple 10 implanted to repair a fracture F between two bone fragments A and B. To repair the fracture, the surgeon initially manipulates fragments A and B to bring them substantially together at the fracture site. Next, staple 10 with arms 20,30 spread apart (as shown in FIG. 2) is placed with one of the tips 26,36 of each angled arm resting on each fragment at a desired penetration point and with a striking surface facing outwardly, directly away from the fractured bone. The position of the staple is preferably such that the protrusion opposite the striking surface is located to one side of the fracture F, as will be appreciated from FIGS. 1 and 4. Following placement of the staple in this manner, extensions 24,34 of the angled arms are partially driven or otherwise inserted into the respective fragments A and B until, for example, the uppermost of barbs 27,37 have entered the corresponding fragments. Partial insertion may be accomplished by applying an impact force on the exposed (i.e., outwardly facing) striking surface, and correct location of the sharpened tips 26,36 may be ensured by drilling a small pilot hole at each penetration point. The penetration points may be marked for drilling for tapping lightly on the staple with the aforementioned tips resting at the penetration points. It should be noted that the top barbs of the extensions 24,34 are situated to provide sufficient clearance between the body 12 and bone fragments A and B so that the bone fragments will not interfere with rotation of the body when the extensions are partially implanted.

With the staple partly inserted as just described, the surgeon rotates body 12 in order to draw arms 20,30 axially into the body. The movement of the arms draws the associated bone fragments A and B together at the fracture site. The surgeon continues to rotate body 12 until the bone fragments are held tightly against one another by the compressive force generated by rotation of the staple body. The surgeon selects the actual force to be applied across the fracture site by rotating body 12 through an appropriate number of turns, and he should stop the adjustment process with a striking surface of body 12 facing outwardly away from the fractured bone (and thus fully exposed for striking by an impact tool) and a protrusion facing inwardly toward the fractured bone.

Figure 5:
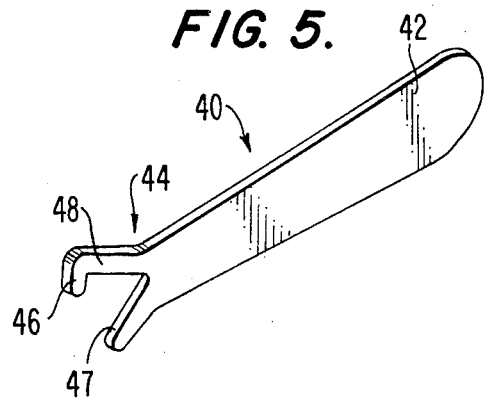
FIG. 5 is a perspective view of a wrench for adjusting the staple.
Figure 6:
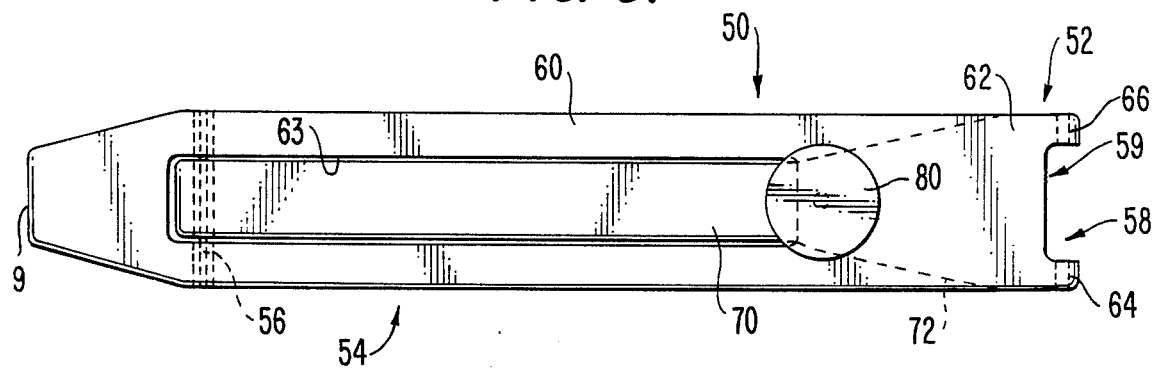
FIG. 6 is a top plan view of a driver tool for use in implanting the staple.

For the purpose of adjusting the staple in the manner just described, a wrench of the form shown in FIG. 5 may be used. The illustrated wrench 40 has a handle 42 joined to a head 44 having jaws 46,47,48 disposed to receive and engage the triangularly arranged striking surfaces.

Once the staple has been fully adjusted to compress the fracture as desired, the surgeon strikes the exposed striking surface using a conventional impactor, for example, to drive the extensions 24,34 further into fragments A and B. The staple should be driven until the protrusion opposite the exposed striking surface embeds beneath the underlying bone surface, as is depicted in FIG. 4. A portion of this bone surface may be osteotomized prior to staple implantation in order to provide a complementary recess for receiving the protrusion. This additional step may be advantageous depending upon the sharpness of the protrusion.

It will be appreciated that the relatively sharp protrusion projecting into the fractured bone acts as a stop to prevent rotation of staple body 12. Thus, the compressive force exerted between bone fragments A and B by the staple will be reliably maintained, and the fracture will heal properly and quickly.

From the preceding discussion, it will be apparent that the presence of a plurality of striking surfaces offers certain advantages in practice. For example, the surfaces provide facets for engagement by a wrench to facilitate rotation of the staple body for adjustment purposes. In addition, a plurality of striking surfaces admits of a finer adjustment capability than a single surface. In the illustrative staple, for instance, for each ⅓ turn of body 12 a striking surface will be exposed for the application of an impactor or the like and a corresponding rotation preventing protrusion will be positioned for receipt beneath an underlying bone surface. Also, with a triangular striking surface arrangement, the planar striking surfaces themselves provide sharp-edged protrusions for embedding beneath the bone surface. The specific striking surface arrangement shown, being limited to an intermediate portion of the staple body, avoids unnecessary bulk of both the staple body and the rotation preventing protrusions.

As was indicated briefly in the introductory summary, it may be desirable in certain applications of the inventive staple to have the angled arms stabilized—more particularly, held fixed against rotation—relative to one another, at least as the staple is initially being inserted. When the angled arms are not secured during insertion of the staple, the opposite ends of the staple might rock in opposite directions when tips 26,36 are resting upon or only slightly inserted into corresponding bone members. A small degree of rotation of the arms on the body axis occurs during this motion. Such rocking can make proper implantation of the staple more difficult. However, when the angled arms are fixed against rotation, the staple presents a rigid structure and cannot rock in the foregoing manner.

FIGS. 6–9 depict a tool for stabilizing the angled arms and for driving the staple into a pair of bone members. In the form shown, the driver, designated by reference numeral 50, has a generally flat clamping head 52 formed by the respective front ends 62,72 of two elongate arm members 60,70. The driver also has a handle 54, formed by rearwardly extending portions of arms 60,70. The rear portion of arm 60 has a central opening 63 in which a narrowed rear end of arm 70 is received and connected to arm 60 by hinge means, such as hinge pin 56 which extends through aligned transverse bores in the arms 60,70, as shown. Thus, clamping head 52 may be opened and closed by pivotal movement of arms 60,70 at the hinged connection just described.

Figure 9:
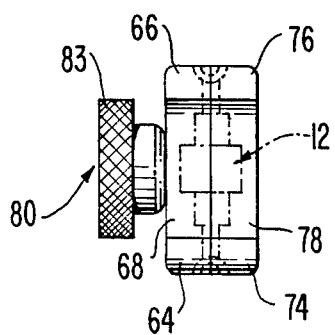
FIG. 9 is a an end view showing a clamping head of the driver tool with the staple received therein.

Addressing the clamping head 52 in more detail, the front end of each arm has two forwardly depending jaws at its opposite sides. Specifically, arm 60 has forwardly depending jaws 64,66 while arm 70 has forwardly depending jaws 74,76, as is best seen in FIG. 9. Jaw pairs 64,74 and 66,76 form two sets of opposed jaws which may be brought together to effect a clamping action. The jaw pairs are aligned with one another and define, respectively, opposite sides of a recess 58 in the clamping head, which recess is configured to receive the staple body 12, as shown. The driver arms have respective end surfaces 68 and 78 extending between the associated depending jaws to define the base 59 of recess 58. The jaw pairs are spaced apart from one another at a distance slightly greater than the length of staple body 12. Thus, when body 12 is positioned within recess 58, arms 20 and 30 are positioned respectively between the two pairs of opposed jaws. Recess base 59 is disposed to rest on the periphery of staple body 12 when the staple is received within clamping head 52. Consequently, an impact force may be applied to the staple body via driver tool 50, as by striking a flat rear end 69 of the tool formed at the rear end of arm 60.

Preferably, the recess base 59 is contoured to conform to the body of the received staple, at least around part of the periphery of the body. Thus, in the case of illustrative staple 10, the recess bottom is generally flat (i.e., surfaces 68 and 78 are generally flat) to engage one of the striking surfaces of the staple body.

Figure 7:
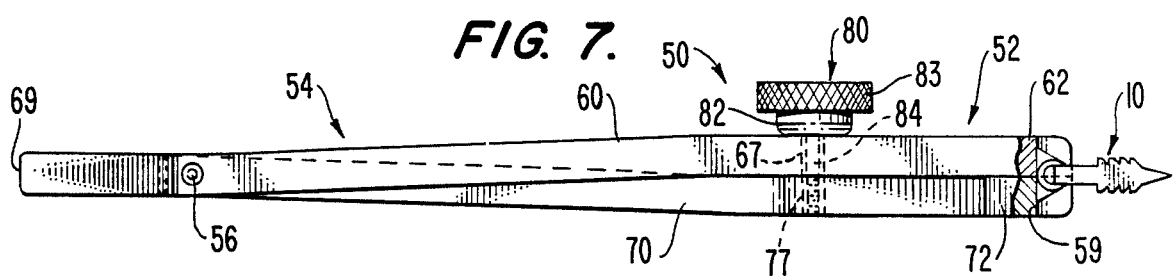
FIG. 7 is a side elevation view of the driver tool with the staple received therein.
Figure 8:
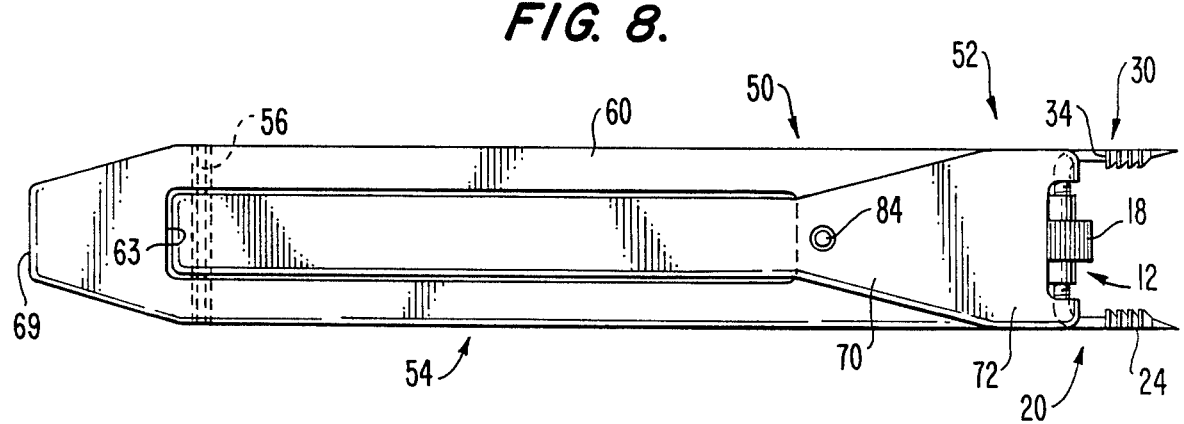
FIG. 8 is a bottom plan view of the driver tool with the staple received therein.

In order to secure the staple arms tightly between the respective pairs of jaws, driver 50 has tightening screw means cooperable between arms 60 and 70. The tightening screw means, as depicted in FIG. 7, may include a bolt 80 having a head 82 situated on top of arm 60 and a shank 84 which extends downward freely through a vertical bore 67 within arm 60 and which has a free end threadably received in a vertical bore 77 within arm 70. Bolt head 82 may have an enlarged portion 82 with a knurled circumference to facilitate rotation of the bolt by hand.

It will be appreciated that staple 10 may be secured within clamping head 52 by loosening bolt 80, inserting the staple body into recess 58 with staple arms 20,30 aligned and projecting forward of the driver and a striking surface resting on base 59 of recess 58, as shown, and then tightening the bolt 80 to draw the front ends 62,72 of arms 60,70 together so that the opposed jaws rigidly clamp the interposed staple arms. The forwardly directed tips of the arms may then be placed at desired bone penetration points, and the staple may be implanted by striking the rear end 69 of the driver. The driver should then be detached from the staple so that the latter may be adjusted, whereupon the staple may be further implanted by striking the exposed striking surface of the staple body, as previously described. Further use of the driver will usually be unnecessary since the staple arms would ordinarily be sufficiently stabilized by the bone members in which they are implanted.

While the invention has been described in the context of its preferred embodiments, it will be apparent to those skilled in the art that various changes and modifications may be made within the principles of the invention, the scope of which is set forth in the appended claims. For example, staple body 12 might be of triangular shape along its entire length. Or, for applications involving the distraction of bone members, the freely extending portions of the angled arms could be serrated only on their outer sides. Alternatively, when the staple is not to be permanently implanted, the extending portions could simply be smooth surfaced. Finally, other applications of the invention besides fracture compression could include arthrodesis (fusion) of small joints, compression fixation of osteotomies, epiphysiodesis (surgical growth arrest) of long bones, and correction of short segment scoliosis curves when anterior fusions are performed. In the latter case, the convex side of the curve would be compressed after the staple arms have been driven into the vertebral bodies.

I claim:

1. Bone staple apparatus for exerting and maintaining a force between two bone members, comprising:
   a body having opposite axially aligned ends threaded axially in opposite directions to one another, a substantially flat peripheral striking surface, and a relatively sharp outward protrusion disposed laterally across said body from said striking surface; and
   a pair of angled arms each having a threaded end portion in axial threaded engagement with a respective one of said axial ends of said body and a free end portion extending substantially perpendicular to the axis of said body for implantation into a bone member.

2. Bone staple apparatus according to claim 1, wherein said striking surface is planar.

3. Bone staple apparatus according to claim 1, wherein said protrusion defines a peripheral edge portion extending axially of said body.

4. Bone staple apparatus according to claim 1, wherein said arms are substantially right angular.

5. Bone staple apparatus according to claim 1, wherein said free end portion is serrated and has a sharpened tip.

6. Bone staple apparatus according to claim 5, wherein said free end portion has a serrated inner side and a smooth outer side.

7. Bone staple apparatus according to claim 1, wherein said body has a plurality of said striking surfaces facing outward of said body in different directions and a plurality of said protrusions, there being one of said protrusions disposed laterally across said body from each of said striking surfaces.

8. Bone staple apparatus according to claim 7, wherein said plurality of striking surfaces includes three striking surfaces defined by respective sides of a portion of said body which is substantially triangular in cross section.

9. Bone staple apparatus according to claim 8, wherein said portion of said body is enlarged and disposed intermediate said opposite ends of said body.

10. Bone staple apparatus according to claim 8, wherein said one protrusion is formed by a junction region of two of said three striking surfaces.

11. Bone staple apparatus according to claim 10, wherein said three striking surfaces are planar, forming sharp edges at their junctions.

12. Bone staple apparatus according to claim 8, in combination with a wrench having a head configured to receive said portion of said body and to engage said striking surfaces for rotating said body.

13. A method of exerting and maintaining a force between two bone members, comprising providing a bone staple including a body having laterally outward protrusion means and axially aligned opposite ends, said ends being threaded axially in opposite directions to one another, and a pair of angled arms each having a threaded end portion in axial threaded engagement with a respective one of said ends of said body and a free end portion extending substantially perpendicular to the axis of said body, partially inserting the free end portions of said arms into said two bone members, respectively, rotating said body to threadably adjust the relative positions of said arms axially of said ends of said body, and further inserting said free end portions within said bone members and embedding said protrusion means beneath a bone surface to prevent further rotation of said body.

14. The method of claim 13, wherein the step of rotating includes turning said body in such a direction as to draw said arms together and compress said bone members against each other.

15. The method of claim 13, wherein the step of rotating includes applying a wrench to a triangular peripheral section of said body and turning said body with said wrench and wherein the step of embedding includes embedding a junction region of two sides of said triangular peripheral section beneath said bone surface.

16. The method of claim 13, wherein the step of further inserting includes subjecting said striking surface to an impact force.

* * * * *